(12) United States Patent
Zhang et al.

(10) Patent No.: US 11,370,727 B1
(45) Date of Patent: Jun. 28, 2022

(54) BENZENE SELECTIVE HYDROGENATION REACTION SYSTEM AND METHOD THEREOF

(71) Applicant: NANJING YANCHANG REACTION TECHNOLOGY RESEARCH INSTITUTE CO., LTD., Nanjing (CN)

(72) Inventors: Zhibing Zhang, Nanjing (CN); Zheng Zhou, Nanjing (CN); Feng Zhang, Nanjing (CN); Lei Li, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN)

(73) Assignee: NANJING YANCHANG REACTION TECHNOLOGY RESEARCH INSTITUTE CO., LTD., Nanjing (CN)

(*) Notice: Subject to any disclaimer, the term of this patent is extended or adjusted under 35 U.S.C. 154(b) by 0 days.

(21) Appl. No.: 17/617,948

(22) PCT Filed: May 28, 2020

(86) PCT No.: PCT/CN2020/092788
§ 371 (c)(1),
(2) Date: Dec. 10, 2021

(87) PCT Pub. No.: WO2021/227135
PCT Pub. Date: Nov. 18, 2021

(30) Foreign Application Priority Data

May 14, 2020 (CN) .......................... 202010406024.2

(51) Int. Cl.
*C07C 5/11* (2006.01)
*B01J 19/24* (2006.01)

(52) U.S. Cl.
CPC ............... *C07C 5/11* (2013.01); *B01J 19/245* (2013.01)

(58) Field of Classification Search
CPC ........... C07C 5/11; C07C 209/36; C07C 5/10; C07C 13/18; C07C 13/20; C07C 29/149;
(Continued)

(56) References Cited

U.S. PATENT DOCUMENTS 5,457,251 A * 10/1995 Yamashita ............... B01J 8/222
585/277

FOREIGN PATENT DOCUMENTS

CN 102241558 A 11/2011
CN 210045217 U 2/2020

* cited by examiner

*Primary Examiner* — Sharon Pregler

(57) ABSTRACT

A benzene selective hydrogenation reaction system and a method are provided. The system includes a benzene refiner, a first hydrogenation reactor, a second hydrogenation reactor and a separator which are connected in sequence. The first hydrogenation reactor is provided with a first inlet and a first outlet, and the second hydrogenation reactor is provided with a second inlet and a second outlet. The first inlet is connected to the discharge port of the benzene refiner; the first outlet is connected to the second inlet; the second outlet is connected to the separator. The catalyst outlet is connected to the first hydrogenation reactor for recycling the catalyst into the first hydrogenation reactor. Two micro-interface units are respectively disposed within the first hydrogenation reactor and the second hydrogenation reactor, and the micro-interface units are used for dispersing and breaking hydrogen into micro-bubbles with a micron-scale diameter.

8 Claims, 1 Drawing Sheet

(58) Field of Classification Search
CPC ....... C07C 29/80; C07C 35/08; C07C 49/403; C07C 15/04; B01J 2208/00725; B01J 8/02; B01J 19/0066; B01J 19/1806; B01J 2219/00006; B01J 2219/00779; B01J 8/025; B01J 8/20; B01J 19/245; B01J 2208/0084; B01J 29/061; B01J 8/222; B01J 8/228

See application file for complete search history.

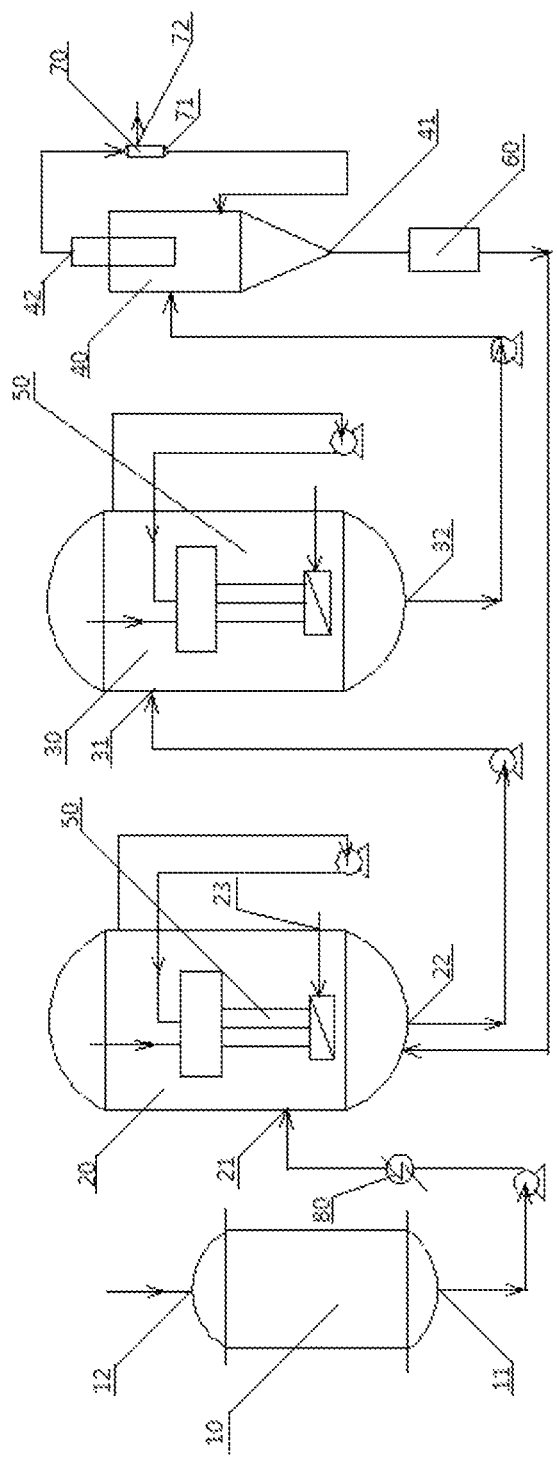

BENZENE SELECTIVE HYDROGENATION REACTION SYSTEM AND METHOD THEREOF

TECHNICAL FILED

The invention relates to the technical field of micro-interface strengthening reactions, in particular, to a benzene selective hydrogenation reaction system and a method thereof.

BACKGROUND OF THE APPLICATION

With the development of synthetic fiber and nylon 66 polyamide industries, benzene selective hydrogenation to prepare cyclohexene has advantages of economy, safety, and environmental protection compared with a conventional benzene complete hydrogenation process, and is an important research in the field of chemical engineering in recent years, and has attracted more and more attention. The existing process for preparing cyclohexene by benzene selective hydrogenation is as follows: performing benzene, hydrogen and a catalyst in two reactors connected in series and with stirring, wherein the reactors are usually bubble oxidation reactors. The bubbles are directly larger than 3 mm or even centimeters, and have a limited phase area at the boundary of the mass. The gas utilization rate is low so that the reaction efficiency is relatively low. In order to strengthen the gas-liquid mass transfer, the bubble reactors are usually provided with additional components such as a tower plate and a static mixer in the tower to enhance the mixing. However, the diameter of the bubbles after mixing is usually 3-30 mm, and the provided phase interface area and mass transfer coefficient (liquid side and gas side) are limited. Therefore, it is relatively difficult to obtain a breakthrough improvement in the reaction performance, thereby affecting the overall efficiency of the reaction. In order to ensure the uniformity of the reaction, the gas, liquid and solid three-phase energy needs to be sufficiently mixed. Therefore, in the prior art, a large stirring is required to ensure the mixing of gas, liquid and solid three-phase, the energy consumption of the reaction is high, and the reaction efficiency is low. In addition, as the reaction efficiency is too high, the energy consumption of cyclohexene and the energy consumption of the system is high, and the energy consumption is high.

In view of this, the present invention is proposed.

SUMMARY

In view of this, the first objective of the present invention is to provide a benzene selective hydrogenation reaction system. In the reaction system, two micro-interface units are disposed within a first hydrogenation reactor and a second hydrogenation reactor. Through the micro-interface units, on the one hand, hydrogen can be dispersed and broken into micro-bubbles with a diameter of micron, the interfacial area between the hydrogen and a liquid phase material is increased, mass transfer space is fully filled, the residence time of the hydrogen in the liquid phase is increased, and the consumption of hydrogen is reduced, thereby greatly improving the reaction efficiency, and significantly reducing the energy consumption of the reaction process; on the other hand, the reaction temperature and the reaction pressure are reduced, thereby improving the yield of cyclohexene, reducing energy consumption, and improving the safety of the system.

A second objective of the present invention is to provide a method for performing a reaction by using the abovementioned reaction system. The method has a mild operation condition, reduces the temperature and pressure of the reaction while ensuring the reaction efficiency, and has high safety performance and low energy consumption, thereby achieving a better reaction effect than the prior art.

In order to achieve the above objectives of the present invention, the following technical schemes are specially adopted.

A benzene selective hydrogenation reaction system is proposed in the present invention, which includes a benzene refiner, a first hydrogenation reactor, a second hydrogenation reactor and a separator which are connected in sequence.

A discharge port is disposed at a bottom of the benzene refiner, the first hydrogenation reactor is provided with a first inlet and a first outlet, and the second hydrogenation reactor is provided with a second inlet and a second outlet. The first inlet is connected to the discharge port of the benzene refiner. The first outlet is connected to the second inlet; the second outlet is connected to the separator for separating a catalyst from a reaction product.

A catalyst outlet is disposed at a bottom of the separator, and the catalyst outlet is connected to the first hydrogenation reactor for recycling the catalyst into the first hydrogenation reactor.

Two micro-interface units are respectively disposed within the first hydrogenation reactor and the second hydrogenation reactor, and the micro-interface units are used for dispersing and breaking hydrogen into micro-bubbles with a micron-scale diameter.

In the prior art, the reaction for preparing cyclohexene by benzene selective hydrogenation has the following problems: on the one hand, the gas-liquid phase mass transfer area of the existing reactor is limited, and during the reaction, the reaction mixed raw materials and hydrogen cannot be sufficiently mixed, the energy consumption is large and the reaction efficiency is low; on the other hand, as the temperature and pressure during the reaction are too high, the number of by-products is increased, and cyclohexene has a low yield, high energy consumption and an increased system risk.

In the benzene selective hydrogenation reaction system of the present invention, micro-interface units are disposed within a first hydrogenation reactor and a second hydrogenation reactor. On the one hand, hydrogen can be dispersed and broken into micro-bubbles with a diameter of micron, the interfacial area between the hydrogen and a liquid phase material is increased, mass transfer space is fully filled, the residence time of the hydrogen in the liquid phase is increased, and the consumption of hydrogen is reduced, thereby greatly improving the reaction efficiency, and significantly reducing the energy consumption of the reaction process. On the other hand, the reaction temperature and pressure are reduced, thereby improving the yield of cyclohexene, reducing energy consumption, and improving the safety of the system.

Further, a raw material benzene inlet is disposed on the top of the benzene refiner, and a discharge port is disposed on the bottom of the benzene refiner. The benzene refiner is provided with a desulfurization adsorbent packing layer, and the benzene refiner can refine the raw material benzene, which is used to remove the sulfur-containing impurities in the raw material benzene. The benzene discharged from the benzene refiner 10 contains sulfur ≤5 ppb, thereby preventing impurities contained in the raw material benzene from poisoning the catalyst.

Further, the first hydrogenation reactor and the second hydrogenation reactor are both fixed-bed catalytic reactors. As the catalyst in the fixed-bed catalyst remains immovable, the catalyst in the bed is not prone to wear and can be used for a long time. In addition, the reactor has a simple structure and is easy to operate.

Further, each of the micro-interface units includes a first micro-interface generator and a second micro-interface generator which are arranged up and down. The first micro-interface generator is connected to a gas guide pipe, a top end of the gas guide pipe extends out of a liquid surface of the first hydrogenation reactor for recovering air, a gas inlet is also disposed on a side wall of the first hydrogenation reactor, and one end of the gas inlet extends into the second micro-interface generator. A structure of the micro-interface units within the second hydrogenation reactor is the same as a structure of the micro-interface units within the first hydrogenation reactor.

Further, the first micro-interface generator is a hydraulic micro-interface generator, and the second micro-interface generator is a pneumatic micro-interface generator. A support member for supporting each other is disposed between the first micro-interface generator and the second micro-interface generator. It can be understood that the specific material, shape and number of the support member are not limited, as long as a support effect can be achieved. Preferably, the support member is tubular, rod-shaped or plate-shaped.

Hydrogen is introduced into the interior of the second micro-interface generator and is dispersed and broken into micron-scale micro-bubbles, thereby effectively increasing mass transfer area between hydrogen and liquid-phase materials, reducing mass transfer resistance, and improving reaction efficiency.

It can be understood by a person skilled in the art that the micro-interface generator used in the present invention is embodied in the prior patents of the present inventor, such as patents of application numbers CN201610641119.6, CN 201610641251.7, CN 201710766435.0, CN 106187660, CN 105903425 A, CN 109437390 A, CN 205831217 U and CN 207581700 U. The specific product structure and operation principle of a micro-bubble generator (i.e. a micro-interface generator) are introduced in detail in the earlier patent CN 20161064119.6, and the present application document discloses that "the micro-bubble generator comprises a body and a secondary breaking member, a cavity is provided in the body, an inlet in communication with the cavity is provided on the body, first and second ends which are opposite to each other of the cavity are open, and the cross-sectional area of the cavity decreases from the middle of the cavity to the first and second ends of the cavity; the secondary breaking member is provided on at least one of the first and second ends of the cavity, a part of the secondary breaking member is provided in the cavity, and an annular channel is formed between the secondary breaking member and through holes which are open at two ends of the cavity; and the micro-bubble generator further comprises an inlet pipe and an inlet pipe". It can be determined from the specific structure disclosed in the application document that the specific operation principle thereof is as follows: a liquid tangentially enters a micro-bubble generator by means of a liquid inlet pipe, and the gas is rotated and cut at an ultra-high speed, so that the gas bubbles are broken into micron-scale micro-bubbles, thereby improving the mass transfer area between a liquid phase and a gas phase; in addition, the micro-bubble generator in the present patent belongs to an air-operated micro-interfacial generator.

In addition, it is disclosed in the earlier patent 201610641251.7 that the primary bubble breaker has a circulating liquid inlet, a circulating gas inlet and a gas-liquid mixture outlet, and the secondary bubble breaker is in communication with the feeding inlet with the gas-liquid mixture outlet, which indicates that the bubble breaker needs gas-liquid mixture to enter. In addition, it can be determined from the following figures that the primary bubble breaker mainly uses the circulating liquid as a motive power, and thus the primary bubble breaker belongs to a hydraulic micro-interface generator, and the secondary bubble breaker simultaneously introduces the gas-liquid mixture into an ellipsoidal rotary ball to rotate, thereby achieving bubble breaking during the process of rotation, and therefore the secondary bubble breaker actually belongs to a gas-liquid linkage micro-interface generator. In fact, either a hydraulic micro-interface generator or a gas-liquid linkage micro-interface generator is a specific form of the micro-interface generator. However, the micro-interface generator used in the present invention is not limited to the abovementioned forms, and the specific structure of the bubble breaker disclosed in the previous patent is only one form of the micro-interface generator of the present invention which can be used.

In addition, the earlier patent 201710766435.0 discloses that "the principle of the bubble breaker is high-speed jet to achieve gas collision with each other", and also states that the bubble breaker can be used in a micro-interface strengthening reactor to prove the correlation between the bubble breaker and the micro-interface generator. Furthermore, in the earlier patent CN 106187660, there is also a related disclosure of the specific structure of the bubble breaker. For details, see paragraphs [0031]-[0041] in the description and the figure, the specific operation principle of the bubble breaker S-2 is abovementioned in detail. The top of the bubble breaker is a liquid inlet, the side face thereof is a gas inlet, and the liquid phase entering from the top provides a winding power, so as to achieve the effect of breaking into ultra-fine bubbles. In the figure, it can also be determined that the bubble breaker is in a conical structure, and the diameter of the upper portion is larger than that of the lower portion, and the winding power can also be provided better for the liquid phase.

As the micro-interface generator has just been developed at the early stage of the prior patent application, it's named as a micro-bubble generator (CN201610641119.6), a bubble breaker (201710766435.0) in the early stage. With continuous technological improvement, the micro-interface generator is named later, and the micro-interface generator in the present invention is equivalent to the previous micro-bubble generator, bubble breaker, etc., but the names thereof are different.

In conclusion, the micro-interface generator of the present invention belongs to the prior art. Although some bubble breakers belong to a type of a pneumatic bubble crusher, some bubble crushers belong to a type of a hydraulic bubble crusher, and some bubble crushers belong to a type of gas-liquid linkage bubble breaker, the difference between these types is mainly selected according to different operation conditions. In addition, with regard to the connection between the micro-interface generator and the reactor and other devices, the micro-interface generator comprises connection structures and connection positions, which are determined according to the structure of the micro-interface generator, and are not limited thereto.

Further, a pipeline connecting the separator and the first hydrogenation reactor is provided with a catalyst regenerator for removing impurities from the catalyst and recovering the activity of the catalyst. The catalyst regenerator is divided from bottom to top into a gas stripping section, a reaction section and a catalyst settling section, wherein the diameter of the catalyst settling section is greater than that of the reaction section, a heat exchange assembly is provided in the settling section, and the heat exchange assembly may be a serpentine heat exchanger or a tandem heat exchange box heat exchanger.

Further, an oil phase outlet is disposed at the top of the separator, and the oil phase outlet is connected to a membrane filter for separating a catalyst in an oil phase material. A ceramic membrane filter can be selected as the membrane filter. The inorganic ceramic membrane of the core component thereof has excellent thermal stability and pore stability, has high strength, chemical corrosion resistance and good cleaning and regeneration performance, and has the dual advantages of high-efficiency filtration and precise filtration.

Further, a catalyst recovery port is disposed at the bottom of the membrane filter, and the catalyst recovery port is connected to a side wall of the separator for returning a separated catalyst-containing aqueous phase material to the separator. The catalyst-containing aqueous phase material is cleaned of impurities by a catalyst regenerator, and is then returned to the interior of the first hydrogenation reactor to be reused after the activity is restored to a great extent, thereby reducing the loss of the catalyst. Moreover, the catalyst is continuously taken out, regenerated and supplemented, and the high activity and high selectivity are maintained, so that cyclohexene can be produced continuously and stably for a long time.

Further, a side wall of the membrane filter is further provided with a product outlet for discharging the reaction product. After the oil phase material passes through the membrane filter, a small amount of catalyst contained therein is completely separated from the product, thereby improving the purity of the product.

Further, a heat exchanger is provided on the pipeline between the discharge port of the benzene refiner and the first inlet for cooling refined benzene before entering the first hydrogenation reactor. The heat exchanger is a tubular heat exchanger. Compared with other heat exchangers, the tubular heat exchanger has the characteristics of simple and compact structure, low cost, large heat transfer area, good heat transfer effect and the like.

In addition, the present invention also provides a method for performing a benzene selective hydrogenation reaction, comprising the following steps: after hydrogen is dispersed and broken into micro-bubbles, performing a hydrogenation reaction with a refined benzene under an action of the catalyst, and collecting the reaction product after being separated by the catalyst.

Further, the refined benzene is first subjected to heat exchange cooling and then introduced into the interior of the first hydrogenation reactor, and hydrogen is introduced into a micro-interface module disposed within the first hydrogenation reactor, so as to break same into micro-bubbles with a micron diameter. After being dispersed and broken into micro-bubbles, the hydrogen reacts with the refined benzene under the action of a catalyst. The mixture of the reacted material and the catalyst slurry enters the interior of the second hydrogenation reactor, and hydrogen is introduced into micro-interface units disposed in the interior of the second hydrogenation reactor, so as to break them into micro-bubbles with a micron diameter. After being dispersed and broken into micro-bubbles, the hydrogen continues to react with the mixture coming out of the first hydrogenation reactor to obtain a cyclohexene mixture. Subsequently, the cyclohexene mixture enters a separator for separating the catalyst, and then is discharged from a product outlet.

Further, the oximation reaction has a temperature of 110-135° C. and a pressure of 2-2.5 MPa.

Compared with the prior art, the present invention has the following beneficial effects:

In the benzene selective hydrogenation reaction system of the present invention, micro-interface units are disposed within a first hydrogenation reactor and a second hydrogenation reactor. On the one hand, hydrogen can be dispersed and broken into micro-bubbles with a diameter of micron, the interfacial area between the hydrogen and a liquid phase material is increased, mass transfer space is fully filled, the residence time of the hydrogen in the liquid phase is increased, and the consumption of hydrogen is reduced, thereby greatly improving the reaction efficiency, and significantly reducing the energy consumption of the reaction process. On the other hand, the reaction temperature and pressure are reduced, thereby improving the yield of cyclohexene, reducing energy consumption, and improving the safety of the system.

BRIEF DESCRIPTION OF DRAWINGS

By reading the detailed description of the preferred embodiments below, various other advantages and benefits will become clear to those of ordinary skill in the art. The drawings are only used for the purpose of illustrating the preferred embodiments, and are not considered as a limitation to the invention. Also, throughout the drawings, the same reference numerals are used to denote the same components. In the drawings:

FIG. 1 is a structural diagram of a built-in micro-interface aminoxylation reaction system according to an embodiment of the present invention.

DETAIL DESCRIPTION

In order to make the purpose and advantages of the invention clearer, the invention will be further abovementioned below in conjunction with the embodiments. It should be understood that the specific embodiments mentioned here are only used to explain the invention, and are not used to limit the invention.

Based on the embodiments of the present invention, all other embodiments obtained by those of ordinary skill in the art without creative work shall fall within the scope of the present invention. If specific conditions are not indicated in the embodiments, it shall be carried out in accordance with the conventional conditions or the conditions recommended by the manufacturer. The reagents or instruments used without the manufacturer's indication are all conventional products that can be purchased on the market.

It should be understood that in the description of the invention, orientations or position relationships indicated by terms upper, lower, front, back, left, right, inside, outside and the like are orientations or position relationships are based on the direction or position relationship shown in the drawings, which is only for ease of description, rather than indicating or implying that the device or element must have a specific orientation, be constructed and operated in a specific orientation, and therefore cannot be understood as a limitation of the invention. In addition, the terms "first", "second", and "third" are only used for descriptive purposes, and cannot be understood as indicating or implying relative importance.

Further, it should also be noted that in the description of the invention, terms "mounting", "connected" and "connection" should be understood broadly, for example, may be fixed connection and also may be detachable connection or integral connection; may be mechanical connection and also may be electrical connection; and may be direct connection, also may be indirection connection through an intermediary, and also may be communication of interiors of two components. Those skilled in the art may understand the specific meaning of terms in the invention according to specific circumstance.

In order to explain the technical schemes of the present invention more clearly, the following description will be given in the form of specific embodiments.

Embodiment

Referring to FIG. 1, a benzene selective hydrogenation reaction system according to an embodiment of the present invention includes a benzene rectifier 10, a first hydrogenation reactor 20, a second hydrogenation reactor 30 and a separator 40 which are connected in sequence. A discharge port 11 and a raw material benzene inlet 12 are disposed at the bottom of the benzene purifier 10, the first hydrogenation reactor 20 is provided with a first inlet 21 and a first outlet 22, and a second hydrogenation reactor 30 are provided with a second inlet 31 and a second outlet 32. The second inlet 31 is connected to the discharge port 11 of the benzene refiner 10. The first outlet 22 is connected to the second inlet 31. The second outlet 32 is connected to the separator 40 for separating catalyst in a reaction product. Two micro-interface units 50 are respectively disposed within the first hydrogenation reactor 20 and the second hydrogenation reactor 30, and are used for dispersing and breaking hydrogen into micro-bubbles with a micron-scale diameter.

Specifically, each micro-interface unit 50 includes a first micro-interface generator and a second micro-interface generator which are arranged up and down, the first micro-interface generator is connected to a gas guide pipe, the top end of the gas guide pipe extends out of a liquid surface of the first hydrogenation reactor for recovering air. A gas inlet 23 is also disposed on a side wall of the first hydrogenation reactor 20, one end of the gas inlet 23 extends into the second micro-interface generator, and a structure of the micro-interface units 50 in the second hydrogenation reactor 30 is the same as those of the first hydrogenation reactor 20. Preferably, the first micro-interface generator is a hydraulic micro-interface generator, and the second micro-interface generator is a pneumatic micro-interface generator. A support member for supporting each other is disposed between the first micro-interface generator and the second micro-interface generator. It can be understood that the specific material, shape and number of the support member are not limited, as long as a support effect can be achieved. Hydrogen is introduced into the interior of the micro-interface units 50 and is dispersed and broken into micron-scale micro-bubbles, thereby effectively increasing mass transfer area between hydrogen and liquid-phase materials, reducing mass transfer resistance, and improving reaction efficiency.

A catalyst outlet 41 is disposed at the bottom of the separator 40 of this embodiment, and the catalyst outlet 41 is connected to the first hydrogenation reactor 20 for recycling the catalyst into the first hydrogenation reactor 20. The pipeline connecting the separator 40 and the first hydrogenation reactor 20 is further provided with a catalyst regenerator 60. The catalyst-containing aqueous phase material is cleaned of impurities by a catalyst regenerator 60, and is then returned to the interior of the first hydrogenation reactor 20 to be reused after the activity is restored to a great extent, thereby reducing the loss of the catalyst. Moreover, the catalyst is continuously taken out, regenerated and supplemented, and the high activity and high selectivity are maintained, so that cyclohexene can be produced continuously and stably for a long time. The catalyst regenerator 60 is divided from bottom to top into a gas stripping section, a reaction section and a catalyst settling section, wherein the diameter of the catalyst settling section is greater than that of the reaction section, a heat exchange assembly is provided in the settling section, and the heat exchange assembly is a tandem heat exchange box heat exchanger.

In addition, an oil phase outlet 42 is further disposed at the top of the separator 40, and the oil phase outlet 42 is connected to a membrane filter 70 for separating a catalyst in an oil phase material. In this embodiment, the membrane filter 70 is a ceramic membrane filter, and the inorganic ceramic membrane of the core component thereof has excellent thermal stability and pore stability, has high strength, chemical corrosion resistance and good cleaning and regeneration performance, and has the dual advantages of high-efficiency filtration and precise filtration.

A catalyst recovery port 71 is disposed at the bottom of the membrane filter 70, and the catalyst recovery port 71 is connected to a side wall of the separator 40 for returning a separated catalyst-containing aqueous phase material to the separator 40. The side wall of the membrane filter 70 is further provided with a product outlet 72 for discharging the reaction product. After the oil phase material passes through the membrane filter 70, a small amount of catalyst contained therein is completely separated from the product, thereby improving the purity of the product.

In this embodiment, a desulphurization adsorbent filler layer is further disposed in the benzene refiner 10. The benzene refiner 10 can refine the raw material benzene, and is used for removing sulfur impurities in the raw material benzene. The benzene discharged from the benzene refiner 10 contains sulfur ≤5 ppb, thereby preventing impurities contained in the raw material benzene from poisoning the catalyst. In addition, a heat exchanger 80 is disposed on a pipeline between the discharge port 11 and the first inlet 21 of the benzene refiner 10 for cooling refined benzene before entering the first hydrogenation reactor 20. Preferably, the heat exchanger 80 is a tubular heat exchanger. Compared with other heat exchangers, the tubular heat exchanger has characteristics of a simple and compact structure, low costs, a large heat transfer area, and a good heat transfer effect.

In this embodiment, the first hydrogenation reactor 20 and the second hydrogenation reactor 30 are both fixed-bed catalytic reactors. As the catalyst in the fixed-bed catalyst remains immovable, the catalyst in the bed is not prone to wear and can be used for a long time. In addition, the reactor has a simple structure and is easy to operate.

The operation and principles of the benzene selective hydrogenation reaction system of the present invention are briefly abovementioned below.

The hydrogen first enters the micro-interface units 50 by means of the gas inlet 23 to be dispersed and broken into micron-scale micro-bubbles, and the liquid-phase raw material refined benzene enters the first hydrogenation reactor 20. The dispersed and broken micro-bubbles are fully emulsified with the liquid-phase mixed raw material, effectively increasing the mass transfer area of the gas and liquid phases, and reducing the mass transfer resistance.

As the fully emulsified emulsion is subjected to a catalytic reaction inside the first hydrogenation reactor 20 in the presence of a catalyst, a temperature of the first hydrogenation reactor 20 is 110-135° C., and a pressure of the first hydrogenation reactor 20 is 2-2.5 MPa. The mixture of the reacted material and the catalyst slurry enters the interior of the second hydrogenation reactor 30, and hydrogen is introduced into micro-interface units 50 provided in the interior of the second hydrogenation reactor 30, so as to break same into micro-bubbles with a micron diameter. After being dispersed and broken into micro-bubbles, the hydrogen continues to react with the mixture coming out of the first hydrogenation reactor 20 to obtain a cyclohexene mixture. Subsequently, the cyclohexene mixture comes out of the second outlet 32 and enters a separator 40. The oil phase material comes out of the oil phase outlet 42 and enters the membrane filter 70. The product after complete separation of the catalyst is discharged from a product outlet 72. The catalyst-containing aqueous phase material is recovered and active by means of a catalyst regenerator 60 through a catalyst recovery inlet 71, and then is sent back to the first hydrogenation reactor 20 for reuse.

So far, the technical solution of the invention has been abovementioned in conjunction with the preferred embodiments shown in the drawings. However, it is easily understood by those skilled in the art that the protection scope of the invention is obviously not limited to these specific embodiments. Without departing from the principle of the invention, those skilled in the art can make equivalent changes or substitutions to the relevant technical features, which will fall into the protection scope of the invention. The above are only preferred embodiments of the invention rather than limits to the invention. Those skilled in the art may make various modifications and changes to the invention. Any modification, equivalent replacement, improvement and the like made within the spirit and principle of the invention all should be included in the protection scope of the invention.

The invention claimed is:

1. A benzene selective hydrogenation reaction system, comprising a benzene refiner, a first hydrogenation reactor, a second hydrogenation reactor and a separator which are connected in sequence; wherein,
   a discharge port is disposed at a bottom of the benzene refiner, the first hydrogenation reactor is provided with a first inlet and a first outlet, and the second hydrogenation reactor is provided with a second inlet and a second outlet; the first inlet is connected to the discharge port of the benzene refiner; the first outlet is connected to the second inlet; the second outlet is connected to the separator for separating a catalyst from a reaction product;
   a catalyst outlet is disposed at a bottom of the separator, and the catalyst outlet is connected to the first hydrogenation reactor for recycling the catalyst into the first hydrogenation reactor; and
   two micro-interface units are respectively disposed within the first hydrogenation reactor and the second hydrogenation reactor, and the micro-interface units are used for dispersing and breaking hydrogen into micro-bubbles with a micron-scale diameter;
   wherein each of the micro-interface units comprises a first micro-interface generator and a second micro-interface generator which are arranged up and down, the first micro-interface generator is connected to a gas guide pipe, a top end of the gas guide pipe extends out of a liquid surface of the first hydrogenation reactor for recovering air, a gas inlet is also disposed on a side wall of the first hydrogenation reactor, one end of the gas inlet extends into the second micro-interface generator, and a structure of the micro-interface units within the second hydrogenation reactor is the same as a structure of the micro-interface units within the first hydrogenation reactor.

2. The benzene selective hydrogenation reaction system according to claim 1, wherein a pipeline connecting the separator and the first hydrogenation reactor is provided with a catalyst regenerator for removing impurities from the catalyst and recovering an activity of the catalyst.

3. The benzene selective hydrogenation reaction system according to claim 1, wherein an oil phase outlet is disposed at a top of the separator, and the oil phase outlet is connected to a membrane filter for separating the catalyst in an oil phase material.

4. The benzene selective hydrogenation reaction system according to claim 3, wherein a catalyst recovery port is disposed at a bottom of the membrane filter, and the catalyst recovery port is connected to a side wall of the separator for returning a separated catalyst-containing aqueous phase material to the separator.

5. The benzene selective hydrogenation reaction system according to claim 4, wherein a side wall of the membrane filter is further provided with a product outlet for discharging the reaction product.

6. The benzene selective hydrogenation reaction system according to claim 1, wherein a heat exchanger is disposed on a pipeline between the discharge port of the benzene refiner and the first inlet for cooling refined benzene before entering the first hydrogenation reactor.

7. A method for performing a benzene selective hydrogenation reaction by using the benzene selective hydrogenation reaction system according to claim 1, comprising the following steps:
   after the hydrogen is dispersed and broken into the micro-bubbles, performing a hydrogenation reaction with a refined benzene under an action of the catalyst, and collecting the reaction product after being separated by the catalyst.

8. The method for performing a benzene selective hydrogenation reaction according to claim 7, wherein a temperature of the first hydrogenation reactor and the second hydrogenation reactor is 110-135° C., and a pressure of the first hydrogenation reactor and the second hydrogenation reactor is 2-2.5 MPa.

* * * * *